(12) United States Patent
Jung et al.

(10) Patent No.: US 10,105,387 B2
(45) Date of Patent: Oct. 23, 2018

(54) TEMPERATURE SENSITIVE ADHESION PREVENTION COMPOSITION AND USE THEREOF

(71) Applicant: MEDYTOX INC., Chungcheongbuk-do (KR)

(72) Inventors: Hyun Ho Jung, Seoul (KR); Gi Hyeok Yang, Cheonan-si (KR); Chang Hoon Rhee, Seoul (KR); Cheon Soo Lim, Daejeon (KR)

(73) Assignee: Medytox Inc., Gyeonggi-do (KR)

( * ) Notice: Subject to any disclaimer, the term of this patent is extended or adjusted under 35 U.S.C. 154(b) by 0 days.

(21) Appl. No.: 15/328,808

(22) PCT Filed: Jul. 24, 2014

(86) PCT No.: PCT/KR2014/006767
§ 371 (c)(1),
(2) Date: Jan. 24, 2017

(87) PCT Pub. No.: WO2016/013700
PCT Pub. Date: Jan. 28, 2016

(65) Prior Publication Data
US 2017/0202871 A1  Jul. 20, 2017

(30) Foreign Application Priority Data
Jul. 24, 2014  (KR) .................. 10-2014-0094025

(51) Int. Cl.
*A61K 31/77* (2006.01)
*A61L 31/14* (2006.01)
(Continued)

(52) U.S. Cl.
CPC .............. *A61K 31/77* (2013.01); *A61K 31/74* (2013.01); *A61K 47/02* (2013.01); *A61K 47/36* (2013.01);
(Continued)

(58) Field of Classification Search
None
See application file for complete search history.

(56) References Cited

U.S. PATENT DOCUMENTS 6,566,345 B2   5/2003   Miller et al.
6,869,938 B1*  3/2005   Schwartz ............... A61K 47/10
                                                    514/42
(Continued)

FOREIGN PATENT DOCUMENTS

EP    1 773 908 B1    9/2012
JP    2001-526246     12/2001
(Continued)

OTHER PUBLICATIONS

Tang et al., Journal of Food Science—vol. 62, No. 4, 1997, pp. 688-712.*
(Continued)

*Primary Examiner* — Karl J Puttlitz
(74) *Attorney, Agent, or Firm* — Rubin and Rudman LLP

(57) ABSTRACT

Provided are a temperature sensitive adhesion prevention composition and a method for producing the same, the composition comprising a polyethylene oxide (PEO) containing copolymer, a carboxy polysaccharide, and a monovalent cation.

14 Claims, 1 Drawing Sheet

(51) Int. Cl.
*A61K 31/74* (2006.01)
*A61K 47/02* (2006.01)
*A61K 47/36* (2006.01)
*A61L 26/00* (2006.01)
*A61L 31/04* (2006.01)

(52) U.S. Cl.
CPC ......... *A61L 26/0004* (2013.01); *A61L 26/009* (2013.01); *A61L 26/0019* (2013.01); *A61L 26/0023* (2013.01); *A61L 31/041* (2013.01); *A61L 31/14* (2013.01); *A61L 2300/424* (2013.01); *A61L 2300/604* (2013.01); *A61L 2300/802* (2013.01); *A61L 2400/06* (2013.01); *A61L 2400/16* (2013.01)

(56) References Cited

U.S. PATENT DOCUMENTS

| | | |
|---|---|---|
| 9,095,643 B2 | 8/2015 | Choi et al. |
| 2003/0129240 A1 | 7/2003 | Reeve et al. |
| 2009/0196844 A1 | 8/2009 | Choi et al. |

FOREIGN PATENT DOCUMENTS

| | | |
|---|---|---|
| JP | 2009-525122 | 7/2009 |
| KR | 10-2002-0012170 A | 2/2002 |
| KR | 10-20040021411 | 3/2004 |
| KR | 10-20050011891 | 1/2005 |
| KR | 10-2007-0078944 A | 8/2007 |
| KR | 10-2010-0835738 | 5/2008 |
| KR | 10-2008-0096766 A | 11/2008 |
| KR | 10-2010-0056009 | 5/2010 |
| WO | 01/82937 * | 11/2001 |
| WO | WO 01/82937 | 11/2001 |
| WO | WO 2013/176375 A1 | 11/2013 |

OTHER PUBLICATIONS

Tang, J. et al., "Gelling Properties of Gellan Solutions Containing Monovalent and Divalent Cations," Journal of Food Science, 62(4):688-712 (1997), Wiley, United States.
International Search Report of PCT/KR2014/006767 dated Apr. 2, 2015, WIPO, Korea.
English translation of Korean Publication No. 10-20040021411, published on Mar. 10, 2004.
English translation of Korean Publication No. 10-20050011891, published on Jan. 31, 2005.
Extended European Search Report of corresponding EP Patent Appl. No. EP 14898221 dated Jan. 12, 2018.
English translation of Office Action issued in JP 2017-503086, dated Oct. 19, 2017.

* cited by examiner

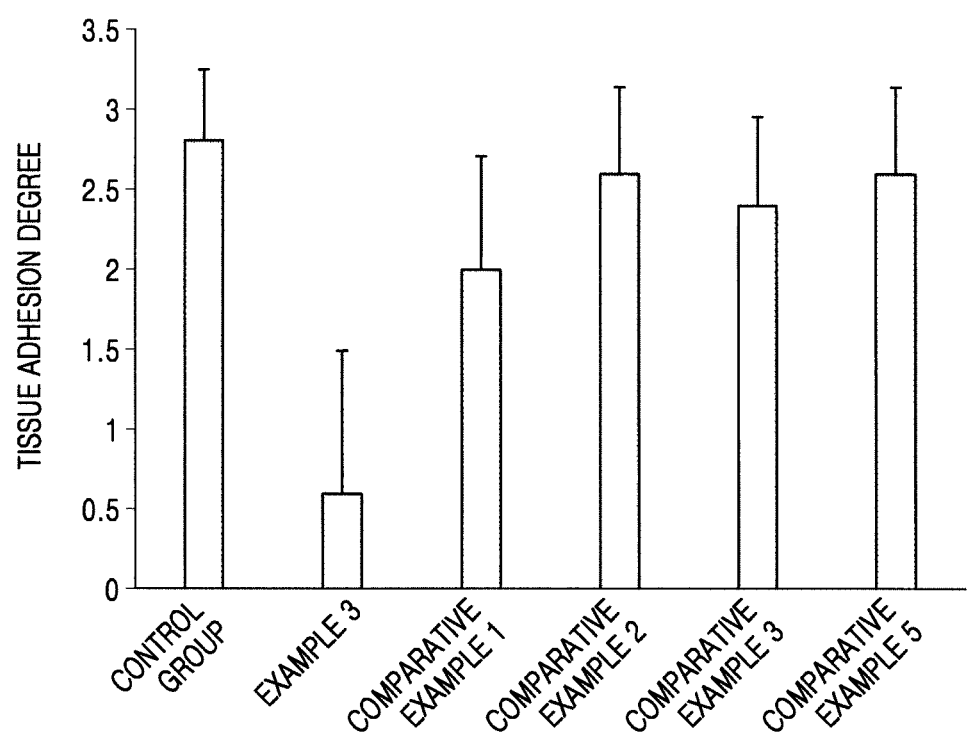

TEMPERATURE SENSITIVE ADHESION PREVENTION COMPOSITION AND USE THEREOF

TECHNICAL FIELD

The present disclosure relates to a temperature-sensitive adhesion prevention composition and use thereof.

BACKGROUND ART

Organ and tissue adhesions frequently occurring after surgery are just one of the natural phenomena that occur during cell proliferation and regeneration in damaged tissues. However, organ and tissue adhesions cause continuous discomfort or dysfunction in patients and require reoperation for adhesiolysis, and even become life-threatening.

Such adhesions occur almost anywhere in the body such as muscle, the sclera, the conjunctiva, a Tenon's capsule, an intermuscular membrane, etc., but it is known that the most clinically severe problems are caused by repeated operations due to peritoneal adhesion or intestinal obstruction following abdominal surgery, excessive bleeding, tissue reaction to suture materials, foreign materials during operation, post-operative inflammation, etc. Therefore, in order to solve postoperative tissue adhesion problems, introducing a physical barrier between an injured tissue and a tissue is a method by which adhesion can be prevented.

To solve postoperative tissue adhesion problems, there have been many attempts to inhibit adhesion between tissues after surgery by using various adhesion inhibitors. Preclude, (W. L. Gore) prepared by using a non-degradable polymer Teflon, Interceed (Johnson & Johnson Medical), prepared by oxidation of a degradable polymer cellulose, Seprafilm (Genzyme), prepared by crosslinking of hyaluronic acid and carboxymethyl cellulose, and Oxiplex (FzioMed), prepared by crosslinking of high-molecular-weight polyethylene oxide and carboxymethyl cellulose, have been used as film-type materials. A non-degradable polymer substantially separates wounds, showing excellent anti-adhesion performance, but exists as a foreign body in the body after an operation, thereby causing inflammation in surrounding tissues or acting as an obstacle to tissue regeneration. Therefore, in some cases, reoperation is required to remove the non-degradable polymer after a certain period of time. A biodegradable polymer is advantageous in that it is degraded and eliminated from the body after a certain period of time, and therefore, does not exist as a foreign body. However, anti-adhesion performance of a degradable polymer is still rather lower than that of a non-degradable polymer. Further, the use of film-type anti-adhesion barriers requires stitching with surrounding tissues using a suture thread in order to prevent movement of the anti-adhesion barrier at the site of application, and the biggest problem is that tissue adhesion frequently occurs at the suture site and it is difficult to introduce film-type anti-adhesion barriers when the site of application is complex, microscopic or tubular-shaped.

To overcome these problems, gel-type carboxymethylcellulose, dextran 70, Flowgel (Mediventures), prepared by using a polyethylene oxide-polypropylene oxide copolymer (Pluronic F127), Adcon-L (Gliatech), based on polylactic acid, Intergel (Lifecore Biomedical), based on hyaluronic acid, AdbA (Amitie), using natural polymers as raw materials, Spraygel (Confluent Surgical), based on spray-type polyethylene oxide, etc., have been developed, of which some are commercially available. However, the gel-type adhesion inhibitors are readily degraded and absorbed by the body (in an aqueous solution) before wounds heal, and thus, they have a problem of exerting low adhesion-preventing effects. Due to this problem, previously used adhesion inhibitors are known to exhibit adhesion-preventing effects of only about 50~70% (J. M. Becker, et al., presented at Clinical Congress of Am. College of Surgeon, New Orleans, Oct. 22, 1995).

U.S. Pat. No. 4,141,973 by Balazs, et al. discloses the use of hyaluronic acid as a main component for inhibiting adhesion. However, as the hyaluronic acid is readily degraded in a living body, it dissolves relatively well, and its half-life in a living body is relatively short, that is, 1 to 3 days, so it cannot be retained in the body for the time necessary to inhibit adhesion, and is severely limited in functioning as an adhesion inhibitor.

U.S. Pat. No. 1,593,394 (product name: Intergel®) discloses a method of improving in vivo stability of a hyaluronic acid polymer by using trivalent ferric chloride (FeCl3), but the FDA has cancelled its registration due to inflammation and adverse effects caused by ferric chloride practically applied as a crosslinking agent in clinical trials.

In U.S. Pat. No. 5,939,485, Bromberg, et al. described a polymer network that had been developed, which is responsive to environmental stimuli, such as pH, temperature, and ionic strength. They used vinyl polymers, acryl polymers, and urethanes, which are non-degradable polymers, in a living body as the structural components of the polymer network, and used polyoxyalkylene polymers and cellulose polymers as the stimuli-sensitive polymers. However, if the non-degradable polymers as described above are used as structural components, they may generate a foreign body reaction because they are not degradable in a living body and have low biocompatibility.

As described above, non-degradable polymers cause inflammation in surrounding tissues, thus requiring reoperation for removal after a certain period of time, and biodegradable polymers have rather low adhesion-preventing effects, as compared with non-degradable polymers. Further, gel-type adhesion inhibitors are readily degraded and absorbed by the body before the wound heal, and thus, they exert low adhesion-preventing effects. Accordingly, there is a demand for a temperature-sensitive adhesion inhibitor to solve the disadvantages of non-degradable polymers and biodegradable polymers.

Poloxamer, a polymer manufactured by BASF, is known as a thermosensitive substance that exists in a solution state at a low temperature but gelates as temperature increases (see U.S. Pat. No. 4,188,373, U.S. Pat. No. 4,478,822 and U.S. Pat. No. 4,474,751). U.S. Pat. No. 5,939,485 by Bromberg, et al. describes that these poloxamers are substances capable of reversible gelation according to stimuli of pH, temperature, and ionic strength. Further, Steinleitner, et al. published an evaluation of the anti-adhesion efficacy of fluid gels having poloxamers as a basic composition [Fertility and sterility 57(2): 305 (1992)].

Generally known poloxamers have a structure of polyethylene oxide (PEO)-polypropylene oxide (PPO)-polyethylene oxide (PEO). For example, Poloxamer 407 has a gelation temperature of about 25° C. and its gelation is influenced by factors such as poloxamer grade, concentration, pH, additives, etc. In addition, the melting temperature of Poloxamer 407 is 56° C. and its specific gravity is 1.05. However, this poloxamer has physical properties such that it forms a polymer gel in aqueous solutions, but is easily dissolved in water. Therefore, poloxamer has a drawback in that it does not retain its gel state in a certain area for a time sufficient to inhibit adhesion.

Korean Patent Nos. 0416104B1 and 0565881B1 describe a method of improving in vivo stability of carboxymethyl cellulose used as a main component and poloxamer by ionic crosslinking of water-soluble alginate with divalent cations ($Ca^{2+}$, $Br^{2+}$, etc.). However, when this method is used, in vivo stability is slightly improved, but, in practice, tissue adhesiveness is reduced at the site of application and the applied solutions flow down from the tissues. Because of this problem, there are restrictions on the use of poloxamers in the peritoneal cavity/pelvic cavity/uterine cavity, which are the most common surgical sites among all surgical sites (about 50% or more), and poloxamers also have low adhesion-preventing effects.

Due to these problems, a variety of film-, fabric-, or gel-type adhesion inhibitors have been developed or commercialized, and until now have been clinically used, but products showing successful adhesion-preventing effects at all surgical sites have not yet been developed. Accordingly, there is a demand for the development of an ideal adhesion inhibitor which has superior biocompatibility, tissue adhesiveness, bioabsorbability, in-body stability, etc., and may be readily applied to all surgical sites.

DETAILED DESCRIPTION OF THE INVENTION

Technical Problem

In order to solve the above problems, the present inventors prepared and completed a temperature-sensitive adhesion inhibitor which is a mixed form of a polyethylene oxide-containing block copolymer having adhesion prevention efficacy and a reversible sol-gel phase transition behavior in response to temperature and a kind of carboxypolysaccharide which provides adhesiveness to prevent the adhesion inhibitor from flowing down from a wound site in a wet state and to firmly adhere the adhesion inhibitor thereto.

A kind of the block copolymer and a kind of carboxypolysaccharide used in the present invention are reported to have adhesion prevention efficacy, but they flow down from a wound site or are rapidly degraded and absorbed by the body fluid before healing of the wound when applied to intricate sites (curved tissues and organs) in the human body. In the present invention, however, a binding ability between the two polymers is increased by using a small amount of a monovalent cation which is a body component, without using a toxic chemical crosslinking agent or multivalent cations, to increase adhesiveness or in-body stability by up to 2 weeks or longer and to address the problem of inflammation or foreign body reaction caused by use of the chemical crosslinking agent or multivalent cations.

Therefore, an object of the present invention is to provide the most ideal adhesion inhibitor for use in any human body in which surgical procedures are performed, without the problems of inflammation and foreign body reaction, the adhesion inhibitor being prepared by mixing a polyethylene oxide-containing block copolymer capable of providing convenience of application, adhesiveness, in-body stability, and adhesion prevention efficacy, and a carboxypolysaccharide component together with a monovalent cation.

Technical Solution

An aspect provides a temperature-sensitive adhesion prevention composition including a polyethylene oxide-containing copolymer (PEO), a carboxypolysaccharide, and a monovalent cation.

As used herein, the term "adhesion" refers to a phenomenon in which adjacent organs or tissues that should be separated from each other adhere together when fibrous tissues are excessively generated or blood runs out and coagulates during the course of recovery of wounds such as from inflammation, gashes, friction, surgery cuts, etc. The term "use for adhesion prevention" refers to a use for preventing adjacent organs or tissues from adhering together.

The composition may include a polyethylene oxide-containing copolymer (PEO). The polyethylene oxide is hydrophilic. The polyethylene oxide is a polymer consisting of a repeating unit of a compound including —O—CH2-CH2)-. A molecular weight of the polyethylene oxide may be more than about 1,000 Da.

The copolymer may include another component which is copolymerized with the polyethylene oxide. Another component may be one or more, for example, two or three selected from the group consisting of polypropylene oxide (PPO), polylactic acid (PLA), polyglycolic acid (PGA), poly(DL-lactide-co-glycolide) (PLGA), polycaprolactone (PCL), poly(dioxanone) (PDO), PLL (poly-L-lysine), polyethyleneglycol (PEG), and hydroxyethylcellulose (HEC). The copolymer may be a block copolymer. Further, the copolymer may be a poloxamer, for example, a poloxamer consisting of polyethylene oxide(PEO)-polypropylene oxide (PPO)-polyethylene oxide(PEO).

The copolymer may include polyethylene oxide in an amount of 10% by weight to 90% by weight. A sol-gel transition temperature may be controlled by controlling the content ratio of polyethylene oxide.

The composition may be thermosensitive. Therefore, the composition may exhibit a reversible sol-gel phase transition behavior in response to temperature. The composition may transform from a sol state outside the body to a gel state inside the body. Therefore, the composition may function as a barrier for preventing adhesions of tissues surrounding the wound site. Since the composition exists in a sol state at room temperature, it may be injected into the wound site, and after application, the composition is gelated and localized to the wound site to improve the adhesion barrier effects.

The molecular weight of the copolymer may be in a range from 1,000 g/mol to 500,000 g/mol, depending on the properties.

The composition may include carboxypolysaccharide. The carboxypolysaccharide may provide appropriate viscosity, adhesiveness, and in-body stability, when the copolymer is applied to the wound site. The carboxypolysaccharide may provide the composition with adhesiveness to prevent the composition from flowing down from a wound site in a wet state and to firmly adhere the composition thereto. Thus, the composition is adhered to the site, to which the composition is applied during an operation, functions as a physical barrier during healing of the wound, and also protects the wound, thereby exhibiting adhesion-preventing effects.

The carboxypolysaccharide may be one or more selected from the group consisting of hyaluronic acid (HA), alginic acid, carboxymethylcellulose (CMC), keratan sulfate, chitosan, collagen, dextran, gelatin, elastin, and fibrin.

Further, the carboxypolysaccharide may be selected from materials having a molecular weight of 100 kg/mol to 5,000 kg/mol. The molecular weight of the carboxypolysaccharide may be 100 kg/mol to 5,000 kg/mol, 500 kg/mol to 4,000 kg/mol, 1,000 kg/mol to 3,000 kg/mol, or 1,500 kg/mol to 2,500 kg/mol.

The composition may include a monovalent cation. The monovalent cation may induce a hydrogen bond inside the polyethylene oxide-containing copolymer, a hydrogen bond inside the carboxypolysaccharide, and a hydrogen bond between the copolymer and the carboxypolysaccharide. The composition may form a network structure due to the hydrogen bonds, and micelles formed from the copolymer are packed, and therefore, the distance between the micelles may be shortened. As a result, the hydrogen bonds between polyethylene oxide chains in the copolymer may be increased.

Accordingly, the monovalent cation increases the binding between the polyethylene oxide-containing copolymer and the carboxypolysaccharide in the composition to provide an adhesion prevention composition with viscosity and adhesiveness. Further, the hydrogen bonds inside the copolymer and the hydrogen bonds inside the carboxypolysaccharide were increased to improve stability of the composition, thereby prolonging a residence time of a gel.

The monovalent cation may be one or more selected from the group consisting of Li+, Rb+, Fr+, Na+, NO2+, NH4+, H3O+, and K+.

With regard to the composition including the polyethylene oxide-containing copolymer, the carboxypolysaccharide, and the solution containing the monovalent cation, the content of the copolymer may be 0.1% by weight to 0.4% by weight, based on 1% by weight of the final composition. If the content of the copolymer is less than 0.1% by weight, based on 1% by weight of the final composition, no sol-gel transition may occur, and if the content of the copolymer is more than 0.4% by weight, based on 1% by weight of the final composition, gelation may occur at room temperature.

When gelation occurs at room temperature, a problem may occur in that contents may not be uniformly applied at the site of application to deteriorate the adhesion prevention efficacy.

Further, the content of the carboxypolysaccharide may be appropriately selected from a range of 0.001% by weight to 0.03% by weight, based on 1% by weight of the final composition, depending on the properties.

If the content of the carboxypolysaccharide is less than 0.001% by weight, based on 1% by weight of the final composition, viscosity and adhesiveness may be decreased and binding ability may also be decreased, and thus it is difficult to provide in-body stability, and if the content of the carboxypolysaccharide is more than 0.03% by weight, based on 1% by weight of the final composition, it is difficult to prepare the final composition because of excessively high viscosity, and also difficult to uniformly apply the composition to the wound site.

The content of the solution containing the monovalent cation may be appropriately selected from 0.001% by weight to 0.02% by weight, based on 1% by weight of the final composition, depending on the properties. If the content of the monovalent cation is less than 0.001% by weight, based on 1% by weight of the final composition, a weak hydrogen bond is formed, thereby decreasing stability of the final composition, and therefore, the composition may be degraded and absorbed before healing of the wound. If the content of the monovalent cation is more than 0.02% by weight, based on 1% by weight of the final composition, too strong a hydrogen bond is formed, and therefore, a portion of the composition may be precipitated or suspended.

Another aspect of the present invention provides a method for producing the adhesion prevention composition, the method including providing the polyethylene oxide(PEO)-containing copolymer, the carboxypolysaccharide, and the cation. The composition may be applied in the form of a liquid or film powder.

With regard to the method, the polyethylene oxide-containing copolymer and the carboxypolysaccharide are the same as described above.

With regard to the method, the cation may be a monovalent cation. The monovalent cation may be one or more selected from the group consisting of Li+, Rb+, Fr+, Na+, NO2+, NH4+, H3O+, and K+.

Further, in the providing of the cation, a solution containing the cation in a particular weight ratio is provided, and the content of the solution may be 0.001 parts by weight to 0.02 parts by weight, for example, 0.002 parts by weight to 0.02 parts by weight, 0.003 parts by weight to 0.02 parts by weight, 0.004 parts by weight to 0.02 parts by weight, 0.004 parts by weight to 0.02 parts by weight, 0.005 parts by weight to 0.02 parts by weight, 0.006 parts by weight to 0.02 parts by weight, 0.007 parts by weight to 0.02 parts by weight, 0.008 parts by weight to 0.02 parts by weight, 0.009 parts by weight to 0.02 parts by weight, 0.010 parts by weight to 0.02, 0.011 parts by weight to 0.02 parts by weight, 0.012 parts by weight to 0.02 parts by weight, 0.013 parts by weight to 0.02 parts by weight, 0.014 parts by weight to 0.02 parts by weight, or 0.015 parts by weight to 0.02 parts by weight, based on 1 part by weight of the final composition. Further, provided is the copolymer or the carboxypolysaccharide at a particular weight ratio, based on the composition. The content of the copolymer may be 0.1 parts by weight to 0.4 parts by weight, based on 1 part by weight of the final composition. The content of the carboxypolysaccharide may be 0.001 parts by weight to 0.04 parts by weight, based on 1 part by weight of the final composition.

Advantageous Effects of the Invention

According to a temperature-sensitive adhesion prevention composition according to an aspect of the present invention, the composition may be provided with a thermosensitive property of reversible sol-gel phase transition, and readily introduced into any site in which surgical procedures are performed. Further, one or more carboxypolysaccharides are used to increase viscosity and tissue adhesiveness of the composition to prevent the composition from flowing down from a surface of the wound at an application site, and to adhere the composition stably thereto. Further, a monovalent cation is used to induce hydrogen bonds in the composition to allow the composition to form a network structure, and thus, low-molecular-weight copolymer micelles are packed to shorten the distance between the micelles. As a result, the hydrogen bonds between polyethylene oxide chains may be increased to improve in-body stability. Furthermore, the composition includes no chemical crosslinking agent to solve the problem of inflammation, thereby achieving in-body safety of the composition.

According to a method for producing the temperature-sensitive adhesion prevention composition according to another aspect of the present invention, a temperature-sensitive adhesion prevention composition provided with stability, viscosity, tissue adhesiveness, and safety may be prepared.

BRIEF DESCRIPTION OF THE DRAWINGS

FIG. 1 shows the result of evaluating tissue adhesions using an adhesion test system according to 4 grades of tissue adhesion severity (if the score of 0, 1, 2, or 3 is higher, adhesion is more severe).

EXAMPLES

Hereinafter, the present invention will be described in more detail with reference to Examples. However, these Examples are for illustrative purposes only, and the scope of the present invention is not intended to be limited by these Examples.

Examples 1-5: Preparation of Temperature-Sensitive Adhesion Prevention Composition A thermosensitive composition was prepared using components and contents as described in the following Table 1 as raw materials. In detail, sodium chloride (NaCl) and hyaluronic acid (HA) were serially dissolved in an ultrapure water, and stirred using a homogenizer. Then, poloxamers (poloxamer 188/poloxamer 407, P188/407 at a weight ratio of (4/6)) were added thereto at a predetermined ratio and content, and dissolved at 20° C. or lower using the homogenizer to prepare a thermosensitive composition solution including poloxamer, hyaluronic acid, and sodium chloride.

TABLE 1

| Component | Content | | | | |
|---|---|---|---|---|---|
| (w/w %) | Example 1 | Example 2 | Example 3 | Example 4 | Example 5 |
| Hyaluronic acid | 0.5 | 0.5 | 0.5 | 0.5 | 0.5 |
| Poloxamer (188/407) | 32 (4/6) | 32 (4/6) | 32 (4/6) | 32 (4/6) | 32 (4/6) |
| NaCl | 2 | 1.5 | 1 | 0.5 | 0.25 |

Comparative Examples 1-5: Preparation of Temperature-Sensitive Adhesion Prevention Composition A thermosensitive composition was prepared in the same manner as in Examples 1-5, except that each component was used in an amount shown in the following Table 2.

TABLE 2

| Component | Content | | | | |
|---|---|---|---|---|---|
| (w/w %) | Comparative Example 1 | Comparative Example 2 | Comparative Example 3 | Comparative Example 4 | Comparative Example 5 |
| Hyaluronic acid | 0.5 | 0.5 | 0 | 0.5 | 0 |
| Poloxamer (188/407) | 32 (4/6) | 0 | 32 (4/6) | 0 | 32 (4/6) |
| NaCl | 0 | 0.5 | 0.5 | 0 | 0 |

Comparative Examples 6: Preparation of Temperature-Sensitive Adhesion Prevention Composition Using Multivalent Ions A thermosensitive composition was prepared in the same manner as in Examples 1-5, except that each component was used in an amount shown in the following Table 3.

TABLE 3

| Component | Content | | | | |
|---|---|---|---|---|---|
| (w/w %) | Comparative Example 6 | Comparative Example 7 | Comparative Example 8 | Comparative Example 9 | Comparative Example 10 |
| Hyaluronic acid | 0.5 | 0.5 | 0.5 | 0.5 | 0.5 |
| Poloxamer (188/407) | 32 (4/6) | 32 (4/6) | 32 (4/6) | 32 (4/6) | 32 (4/6) |
| $CaCl_2$ | 1 | 0.5 | 0.1 | 0.05 | 0.01 |

Examples 6-9: Preparation of Temperature-Sensitive Adhesion Prevention Composition A thermosensitive composition was prepared in the same manner as in Examples 1-5, except that each component was used in an amount shown in the following Table 4.

TABLE 4

| Component | Content | | | | |
|---|---|---|---|---|---|
| (w/w %) | Example 6 | Example 7 | Example 4 | Example 8 | Example 9 |
| Hyaluronic acid | 0.5 | 0.5 | 0.5 | 0.5 | 0.5 |
| Poloxamer (188/407) | 9 (4/6) | 20 (4/6) | 32 (4/6) | 40 (4/6) | 50 (4/6) |
| NaCl | 0.5 | 0.5 | 0.5 | 0.5 | 0.5 |

Experimental Example 1: Observation of Precipitation of Temperature-Sensitive Adhesion Prevention Composition The temperature-sensitive adhesion prevention compositions prepared in Examples 1-5 and Comparative Examples 1-5 were observed for precipitation and the results are shown in Table 6.

As shown in Table 3, no precipitation was observed in the compositions of Examples 3 to 5, that is, each composition including NaCl of 1% by weight, 0.5% by weight, or 0.25% by weight, hyaluronic acid, and poloxamer. In contrast, precipitation was observed in the compositions of Examples 1 and 2, that is, each composition including NaCl of 2% by weight or 1.5% by weight, hyaluronic acid, and poloxamer. These results suggest that when a mixing ratio of NaCl is more than 1.5% by weight in a composition including hyaluronic acid, poloxamer, and NaCl, strong inter-hydrogen bonds between hyaluronic acid and poloxamer, and strong intra-hydrogen bonds inside hyaluronic acid and poloxamer are formed, causing precipitation of some of the compositions.

TABLE 6

| | Presence or absence of precipitation | | Presence or absence of precipitation |
|---|---|---|---|
| Example 1 | Presence | Comparative Example 1 | Absence |
| Example 2 | Presence | Comparative Example 2 | Absence |
| Example 3 | Absence | Comparative Example 3 | Absence |

TABLE 6-continued

| | Presence or absence of precipitation | | Presence or absence of precipitation |
|---|---|---|---|
| Example 4 | Absence | Comparative Example 4 | Absence |
| Example 5 | Absence | Comparative Example 5 | Absence |

Experimental Example 2: Measurement of Gel Residence Time

Each composition prepared in Examples 1-5 and Comparative Examples 1-5 was added to a 1-ml vial, and 1 ml of a phosphate buffer solution (pH 7.4) was added thereto. Then, the phosphate buffer solution on the surface layer of the gel was removed at a predetermined time once a day while storing the vials in an incubator at 37° C., and the residual volume was observed to measure a gel residence time. The results are shown in Table 7.

As shown in Table 7, gel residence times of Examples 3 to 5 were 14 days and 10 days, which were longer than those of Comparative Examples.

Example 1 and Example 2 were excluded from observation, because of precipitation. In the case of Examples 3 to 5, % by weight of each of the solutions containing monovalent cations was 1, 0.5, and 0.25 w/w %. In the case of Comparative Example 1 containing no NaCl, the gel residence time was 8 days, which was shorter than those of Examples 3 to 5. Therefore, the solutions containing cations of 0.1% by weight to less than 1.5% by weight were found to improve the gel residence time of the composition.

These results suggest that the polyethylene oxide-containing copolymer/carboxypolysaccharide compositions having a particular content of monovalent cations increase hydrogen bonds inside the copolymer, hydrogen bonds inside the carboxypolysaccharide, and hydrogen bonds between the copolymer and the carboxypolysaccharide, thereby improving stability of the composition.

Further, referring to Comparative Example 3 and Examples 3 to 5, it was confirmed that presence of a hydroxy polysaccharide such as hyaluronic acid further increases the gel residence time of the composition.

TABLE 7

| | Gel residence time (day) | | Gel residence time (day) |
|---|---|---|---|
| Example 1 | — | Comparative Example 1 | 8 |
| Example 2 | — | Comparative Example 2 | 2 |
| Example 3 | 14 | Comparative Example 3 | 6 |
| Example 4 | 14 | Comparative Example 4 | 1 |
| Example 5 | 10 | Comparative Example 5 | 5 |

Experimental Example 3: Test of Precipitation and Gel Residence Time of Temperature-Sensitive Adhesion Prevention Composition Using Multivalent Cations Precipitation and gel residence time of the multivalent cation-containing compositions prepared in Comparative Examples 6-10 were examined and the results are shown in Table 8.

As shown in Table 8, precipitation of the compositions of Comparative Examples 6 to 10 was observed, that is, each composition including CaCl2 of 1% by weight, 0.5% by weight, 0.1% by weight, or 0.05% by weight, hyaluronic acid, and poloxamer. In contrast, no precipitation of the composition of Comparative Example 10 was observed, that is, the composition including CaCl2 of 0.01% by weight, hyaluronic acid, and poloxamer. The composition of Comparative Example 10 showing no precipitation was observed according to the method of measuring the gel residence time as in Experimental Example 2, and as a result, the compositions of Comparative Example 6-10 showed gel residence times similar to that of the composition of Example 6 containing no monovalent cation. These results suggest that use of the divalent cation CaCl2 did not improve the gel residence time. It was confirmed that the monovalent cation of the present invention effectively improves binding ability between the polyethylene oxide-containing copolymer and the carboxypolysaccharide polymer, thereby increasing the gel stability.

TABLE 8

| | Presence or absence of precipitation | Gel residence time |
|---|---|---|
| Comparative Example 6 | Presence | — |
| Comparative Example 7 | Presence | — |
| Comparative Example 8 | Presence | — |
| Comparative Example 9 | Presence | — |
| Comparative Example 10 | Absence | 8 |

Experimental Example 4: Measurement of Sol-Gel Phase Transition Temperature

Sol-gel transition temperatures of the compositions prepared in Examples 4 and 6-9 were measured. Each composition was added to a vial, the vials were stored in a refrigerator at about 4° C. for 30 minutes, and then each sample in a sol state was added to a 50-ml vial. The vials were placed in a circulating water bath, and a temperature at which viscosity of the composition was rapidly changed, that is, a temperature at which flowability of the composition disappeared while a temperature of the water bath was slowly raised was determined as a lower critical solution temperature (LCST). Each composition prepared in Examples 4 and 6-9 was measured in the same manner and the results are shown in Table 9.

As shown in Table 9, it was confirmed that the composition of Example 6, that is, the composition including a polyethylene oxide-containing copolymer, which is a poloxamer, in an amount of 0.09% by weight or less, based on 1% by weight of the final composition, showed no sol-gel transition. It was also confirmed that the composition of Example 8, that is, the composition including the polyethylene oxide-containing copolymer, which is a poloxamer, in an amount of 0.4% by weight or more, based on 1% by weight of the final composition, showed sol-gel transition at a temperature lower than room temperature. Based on the results of Table 9, it can be seen that sol-gel phase transition occurs at a particular temperature according to the content of the polyethylene oxide-containing copolymer, which is a poloxamer having a property of temperature sensitivity.

TABLE 9

| | Sol-gel phase transition temperature (° C.) |
|---|---|
| Example 6 | — |
| Example 7 | 60 |
| Example 4 | 31 |
| Example 8 | 10 |
| Example 9 | — |

Experimental Example 5: Test of Adhesion Prevention Efficacy in Animals

An animal test (cecum/abdominal wall abrasion rat model) was performed to evaluate tissue adhesion prevention efficacy, using a control group, in which no materials were added between the wound sites after administration of each composition of Example 3 and Comparative Examples 1-3 and 5.

In the animal test, 5 SD rats (female) per group were used. First, ketamine (60~100 mg/kg) and xylazine (5~10 mg/kg) were mixed and then the rats were anesthetized by injecting them with the mixture intraperitoneally. The abdominal hairs of the anesthetized rats were shaved and disinfected with povidone, and a 4~5 cm-long midline laparotomy was performed. The cecum was taken out and a wound of size 1 cm×1 cm was formed in the surface of the cecal serosa using a bone burr until the serosal surface was hemorrhagic, and the adjacent abdominal wall was wounded using a 15T blade such that the epidermis was peeled off. The two abraded sites faced each other and no treatment was performed in the control group, and then the abdominal wall and skin layers were sutured successively. To the experimental groups, each prepared adhesion prevention composition (Example 3, Comparative Examples 1-3, 5) was uniformly applied to the abraded sites in the cecum and the abdominal wall, and then the abdominal wall and the skin layers were sutured successively.

At 10 days after surgery, tissue adhesions were examined. The results of evaluating tissue adhesions using an adhesion test system according to 4 grades of tissue adhesion severity (if the score of 0, 1, 2, or 3 is higher, adhesion is more severe) are shown in FIG. 1. As shown in FIG. 1, it was confirmed that Example 3 showed remarkably excellent adhesion prevention efficacy, as compared with Comparative Examples 1-3, and 5. Further, as shown by the gel residence time results of Experimental Example 2, it was also confirmed that as the gel residence time increased, the adhesion prevention efficacy was more excellent. Accordingly, it was confirmed that the composition including poloxamer, which is a polyethylene oxide-containing copolymer, and hyaluronic acid, which is a kind of carboxypolysaccharide, together with a monovalent cation, from sodium chloride, showed a gel residence time of 10 days or longer, and also superior adhesion prevention efficacy in the animal test.

What is claimed:

1. An adhesion prevention composition comprising a polyethylene oxide(PEO)-comprising copolymer, a carboxypolysaccharide, and a monovalent cation, wherein the composition is capable of transitioning from sol state to gel state upon raising temperature and does not contain a multivalent cation.

2. The adhesion prevention composition of claim 1, wherein the monovalent cation is one or more selected from the group consisting of Li+, Rb+, Fr+, Na+, NO2+, NH4+, H3O+, and K+.

3. The adhesion prevention composition of claim 1, wherein the copolymer comprises polyethylene oxide in an amount of 10% by weight to 90% by weight.

4. The adhesion prevention composition of claim 1, wherein the copolymer comprises another component which is copolymerized with the polyethylene oxide, another component being one or more selected from the group consisting of polypropylene oxide (PPO), polylactic acid (PLA), polyglycolic acid (PGA), poly(DL-lactide-co-glycolide) (PLGA), polycaprolactone (PCL), and poly(dioxanone) (PDO).

5. The adhesion prevention composition of claim 1, wherein the carboxypolysaccharide is one or more selected from the group consisting of hyaluronic acid, alginic acid, and carboxymethylcellulose.

6. The adhesion prevention composition of claim 1, wherein a weight ratio of the copolymer to the composition is 0.1:1 to 0.4:1.

7. The adhesion prevention composition of claim 1, wherein a weight ratio of the carboxypolysaccharide to the composition is 0.001:1 to 0.03:1.

8. A method for producing an adhesion prevention composition, the method comprising providing a polyethylene oxide(PEO)-comprising copolymer, a carboxypolysaccharide, and a monovalent cation and forming a composition, wherein the composition is capable of transitioning from sol state to gel state upon raising temperature and does not contain a multivalent cation.

9. The method of claim 8, wherein the monovalent cation is one or more selected from the group consisting of Li+, Rb+, Fr+, Na+, NO2+, NH4+, H3O+, and K+.

10. The method of claim 8, wherein the copolymer comprises polyethylene oxide in an amount of 10% by weight to 90% by weight.

11. The method of claim 8, wherein the copolymer comprises another component which is copolymerized with the polyethylene oxide, another component being one or more selected from the group consisting of polypropylene oxide (PPO), polylactic acid (PLA), polyglycolic acid (PGA), poly(DL-lactide-co-glycolide) (PLGA), polycaprolactone (PCL), and poly(dioxanone) (PDO).

12. The method of claim 8, wherein the carboxypolysaccharide is one or more selected from the group consisting of hyaluronic acid, alginic acid, and carboxymethylcellulose.

13. The method of claim 1, wherein a weight ratio of the copolymer to the composition is 0.1:1 to 0.4:1.

14. The method of claim 1, wherein a weight ratio of the carboxypolysaccharide to the composition is 0.001:1 to 0.03:1.

* * * * *